(12) United States Patent
Boesten et al.

(10) Patent No.: US 6,291,701 B1
(45) Date of Patent: Sep. 18, 2001

(54) PROCESS FOR PREPARING OPTICALLY ACTIVE 2-AMINO-ω-OXOALKANOIC ACID DERIVATIVES

(75) Inventors: Wilhelmus H. J. Boesten; Quirinus B. Broxterman; Marcus J. M. Plaum, all of Sittard (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/640,916

(22) Filed: Aug. 18, 2000

Related U.S. Application Data (62) Division of application No. 09/160,342, filed on Sep. 25, 1998, now Pat. No. 6,133,002.
(60) Provisional application No. 60/069,776, filed on Dec. 16, 1997.

(30) Foreign Application Priority Data

Sep. 25, 1997 (NL) .................................................. 1007113

(51) Int. Cl.$^7$ ............................................... C07C 255/11
(52) U.S. Cl. ........................................................ 558/448
(58) Field of Search ............................................ 558/448

(56) References Cited

U.S. PATENT DOCUMENTS

| 4,376,864 | 3/1983 | Drauz | 549/373 |
|---|---|---|---|
| 4,424,370 | 1/1984 | Kleemann | 549/373 |
| 5,332,826 | 7/1994 | Buckland | 546/330 |
| 5,409,946 | 4/1995 | Garvey | 514/372 |

FOREIGN PATENT DOCUMENTS

| 37 02943 | 8/1987 | (DE) . |
|---|---|---|
| 0 052 200 | 9/1981 | (EP) . |
| 0 052 201 | 9/1981 | (EP) . |
| 0 179 523 | 4/1986 | (EP) . |
| 0 307 023 | 8/1988 | (EP) . |
| 0 383 403 | 2/1990 | (EP) . |
| 0 629 627 | 6/1994 | (EP) . |
| 0 672 665 | 3/1995 | (EP) . |
| 1 548 032 | 8/1976 | (GB) . |
| 48 039 416 | 6/1973 | (JP) . |

OTHER PUBLICATIONS

Doelz et al., "Allysine Peptides and Derivatives", Int. J. Peptide Protein Res. (1988), pp. 307–320.
Rumbero et al., "Chemical Synthesis of Allysine Ethylene Acetal and Conversion in sutu Into 1–Piperideine–6–carboxylic Acid: Key Intermediate of the $_α$–Aminoadipic Acid for β–Lactam Antibiotics Biosynthesis", Biorganic & Medicinal Chemistry, vol. 3, No. 9, 1995, pp. 1237–1240.
Sham et al., "Novel Non–basis Bioisostere of Hiidine Synthesized From L–Aspartic Acid", J. Chem. Soc., Chem. Commun., 1987, pp. 1792–1793, vol. 23.

*Primary Examiner*—Laura L. Stockton
(74) *Attorney, Agent, or Firm*—Pillsbury Winthrop LLP (57) ABSTRACT

A process is disclosed for preparing an (S)-2-amino-ω-oxoalkanoic acid derivative in which the corresponding aldehyde is converted into the corresponding acetal-protected aldehyde, the acetal-protected aldehyde is converted into the corresponding aminonitrile, the aminonitrile is converted into the corresponding amino acid amide, the amino acid amide is subjected to an enzymatic, enantioselective hydrolysis in which the (R)-enantiomer of the amino acid amide remains and the (S)-enantiomer is converted into the (S)-amino acid, and the (S)-amino acid is isolated. Preferably, the reaction mixture obtained after the conversion of the aminonitrile into the amino acid amide is treated with a benzaldehyde to form the Schiff base of the amino acid amide. The Schiff base is separated out and is converted into the free amino acid amide.

7 Claims, 6 Drawing Sheets

SAME FOR THE PREPARATION OF D-PROLINE, (LINE 10/11), n=2

PROCESS FOR PREPARING OPTICALLY ACTIVE 2-AMINO-ω-OXOALKANOIC ACID DERIVATIVES

RELATED APPLICATIONS

This application is a division of application Ser. No. 09/160,342, filed Sep. 25, 1998 now U.S. Pat. No. 6,133, 002.

This application is a complete application that claims the benefit of U.S. Provisional Application No. 60/069,776 filed Dec. 16, 1997, the complete disclosure of which is incorporated herein by reference.

FIELD OF THE INVENTION

The invention relates to a process for preparing an optically active 2 amino-ω-oxoalkanoic acid derivative represented by formula 1

(1)

wherein n equals 0, 1, 2, 3, or 4 and $R_1$ and $R_2$ each independently represent an alkyl group with 1–10 carbon atoms or jointly form an alkylene group to thereby form a ring with 3 or 4 carbon atoms together with the oxygen atoms to which they are bound and the carbon atom to which the oxygen atoms are bound. The starting materials for preparing formula 1 are readily commercially available.

BACKGROUND OF THE INVENTION

A preparation of a racemic mixture of a 2-amino-ω-oxoalkanoic acid derivative of formula 1 is described in Biorg. & Med. Chem. (1995) 1237–1240. However, the preparation method described therein proceeds via an 8-step process, starting from 3,4-dihydro-2H-pyran, with various protection and de-protection steps and is hence very laborious.

SUMMARY AND OBJECTS OF THE INVENTION

The invention provides a new, simple method for preparing 2-amino-ω-oxoalkanoic acid derivatives represented by formula 1

(1)

wherein n equals 0, 1, 2, 3, or 4 and $R_1$ and $R_2$ each independently represent an alkyl group with 1–10 carbon atoms or jointly form an alkylene group to thereby form a ring with 3 or 4 carbon atoms together with the oxygen atoms to which they are bound and the carbon atom to which the oxygen atoms are bound. The starting materials for preparing a compound of formula 1 are readily commercially available.

A process is disclosed for preparing an (S)-2-amino-ω-oxoalkanoic acid derivative in which the corresponding aldehyde is converted into the corresponding acetal-protected aldehyde, the acetal-protected aldehyde is converted into the corresponding aminonitrile, the aminonitrile is converted into the corresponding amino acid amide, the amino acid amide is subjected to an enzymatic, enantioselective hydrolysis in which the (R)-enantiomer of the amino acid amide remains and the (S)-enantiomer is converted into the (S)-amino acid, and the (S)-amino acid is isolated. Preferably, the reaction mixture obtained after the conversion of the aminonitrile into the amino acid amide is treated with a benzaldehyde, in which the Schiff base of the amino acid amide is formed, the Schiff base is separated and is converted into the free amino acid amide.

This is achieved according to the invention with a process converting the corresponding aldehyde of formula 2

(2)

wherein n is as described above into the corresponding acetal-protected aldehyde of formula 3

(3)

wherein n, $R_1$ and $R_2$ are as described above, converting the acetal-protected aldehyde into the corresponding aminonitrile of formula 4

(4)

wherein n, $R_1$ and $R_2$ are as described above, converting the aminonitrile into the corresponding amino acid amide of formula 5

(5)

wherein n, $R_1$ and $R_2$ are as described above, subjecting the amino acid amide to an enzymatic, enantioselective hydrolysis in which the (R)-enantiomer of the amino acid amide remains and the (S)-enantiomer is converted into the (S)-amino acid represented by formula (1), and isolating the (S)-amino acid.

It has been discovered that, in spite of the fact that the selectivity in the first step of the process can be relatively low, an economically attractive process can nevertheless be obtained.

The optically active compounds represented of formula 1 are novel and are particularly suitable for use in the preparation of, for example, allysin, an important crosslink precursor in proteins, as described in Int. J. Pept. Protein Res.

(1988), 307–20, and in the preparation of pharmaceuticals, for example as described in EP-A-629627, the complete disclosures of both are incorporated herein by reference.

Allysin can be obtained by an acid catalysed (e.g. an Amberlist -15) deacetylation of a compound of formula 1 with n=3.

Without protection such compound will be immediately converted in the cyclic compound:

Formula (1)
n = 3 →

For use in the peptide synthesis a compound of formula 1 with n=3 is treated with HCl and MeOH in order to obtain (8)

Figure 1:
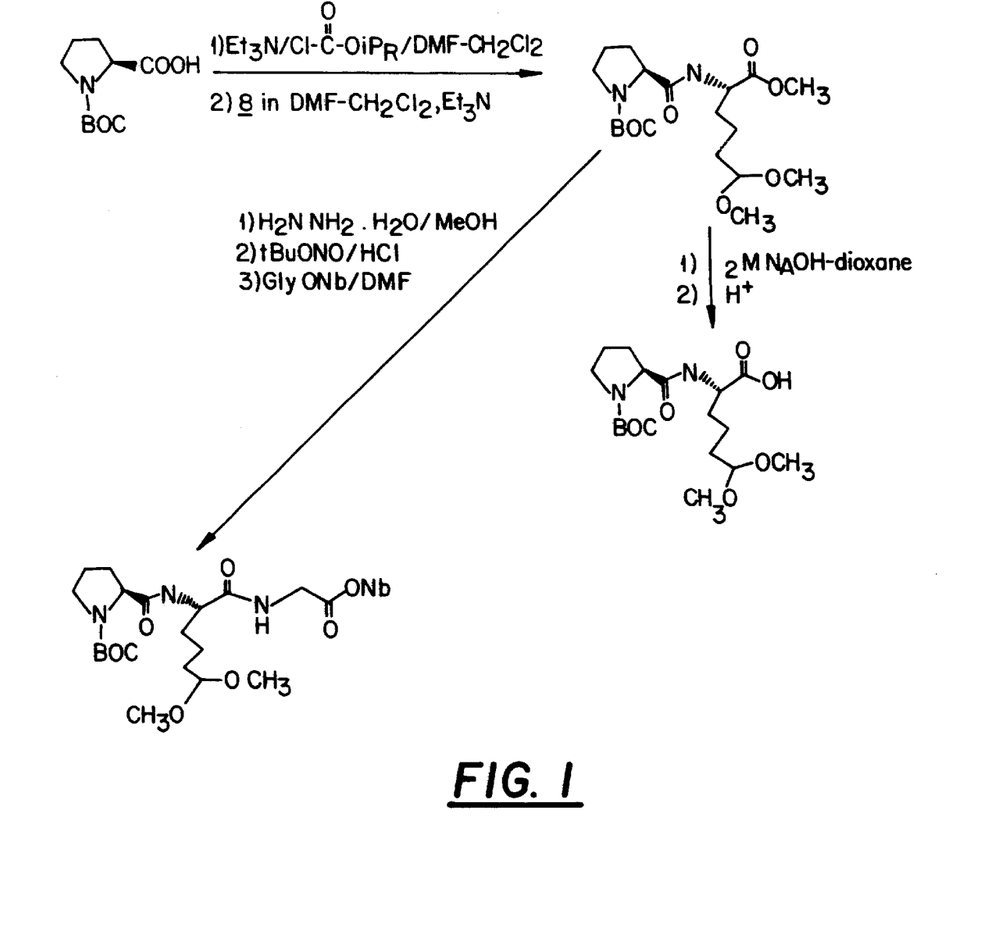
FIG. 1 is a reaction scheme using compound (8) in the synthesis.

An example of peptide chemistry is shown in FIG. 1, using the above compound (8), and is also further described in J. Pept. Protein Res. (1988), 307–20, incorporated by reference above.

Figure 2A:
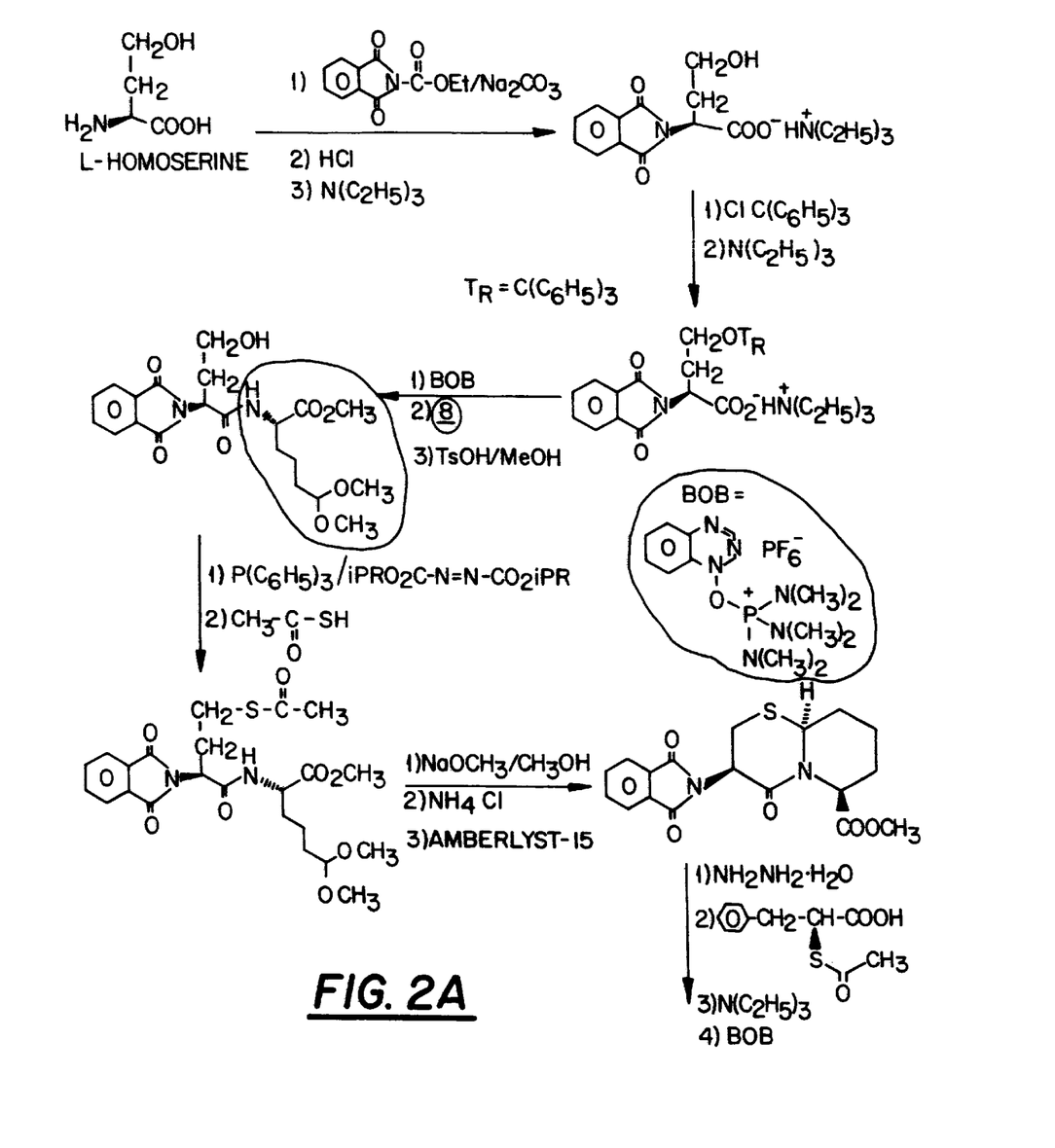
FIG. 2 is a reaction scheme taken from EP-A-629627.
Figure 2B:
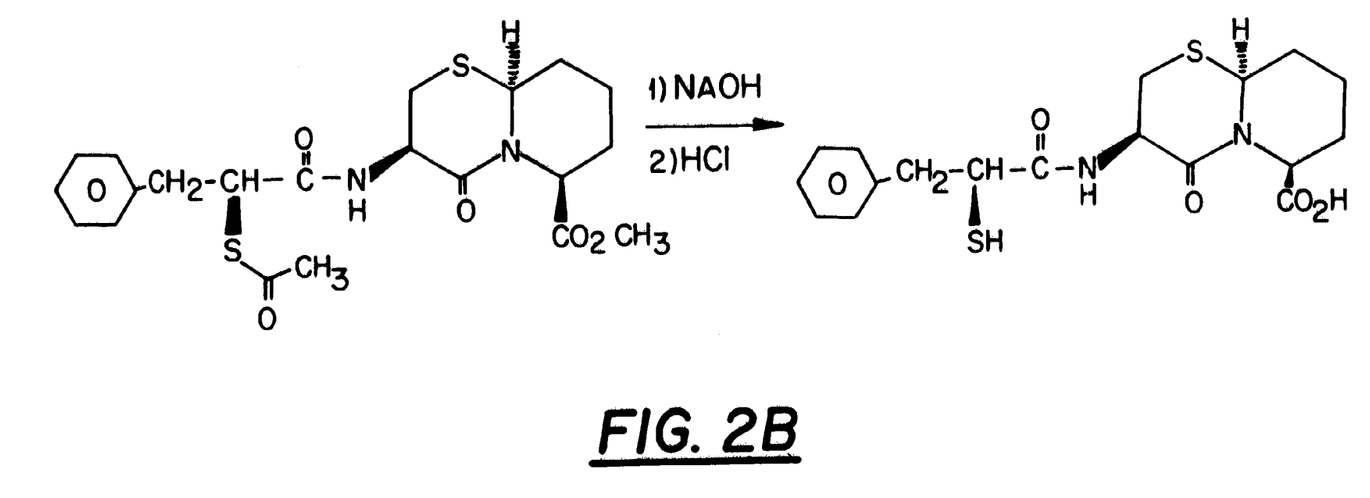

The preparation of a pharmaceutical as referred to above is shown in FIG. 2, and is described in EP-A-629627, incorporated by reference above.

More particularly, in the process according to the invention, one of the two aldehyde functional groups in the aldehyde represented by formula 2 is first protected through conversion, in a manner known per se, into an acetal. cf. T.H. Greene, Protective Groups in Organic Synthesis, John Wiley & Sons, New York (1981). This can for example be done with the aid of an alcohol, for example an alcohol with 1–5 carbon atoms when $R_1$ and $R_2$ represent an alkyl group, or with the aid of a diol with 1 to 5 carbon atoms, in particular a 1,2-ethanediol or a 1,3-propanediol, whether or not substituted with for example an alkyl group with 1–5 carbon atoms, for example 1,2-ethanediol, 1,2-propanediol, 1,3-propanediol or 2,3-butanediol, when $R_1$ and $R_2$ form part of a ring structure; or via re-acetalization, for example with the aid of orthoformate esters.

The acetalization can, for example, be carried out by bringing the aldehyde represented by formula 2 into contact with an alcohol or a diol under acid conditions such as, for example, in the presence of a sulphonic acid, in particular p-toluenesulphonic acid. The acetalization is optionally carried out in the presence of a solvent in principle, any solvent that does not interfere with the reaction can be used as a solvent such as, for example, aromatic hydrocarbons, in particular benzene, toluene and xylene; halogenated hydrocarbons, for example dichloromethane; esters, preferably hindered esters, in particular isopropyl acetate or isobutyl acetate or other esters having bulky ester groups; and ethers, in particular methyl-t-butyl ether (MTBE). The acetalization with an alcohol or diol is preferably carried out at elevated temperature, for example at a temperature of between about 50° C. and about 150° C., preferably at reflux temperature.

The acetal-protected aldehyde obtained is subsequently converted into the corresponding aminonitrile, for example via a Strecker synthesis. cf., J. March, Advanced Organic Chemistry, John Wiley & Sons, New York, pp. 855–856 (3$^{rd}$ Ed. 1981); T. W. Graham Solomons, Fundamentals of Organic Chemistry, John Wiley & Sons, New York, pp. 980–981 (4$^{th}$ Ed. 1994). The acetal-protected aldehyde can, for example, be converted into the aminonitrile in the presence of ammonia with the aid of a cyanide compound, for example HCN, NaCN or KCN.

The aminonitrile compounds represented by formula 4 intermediates are novel compounds. The invention hence also relates to these intermediates. The racemic (R,S)-amide mixture is enantioselectively hydrolysed using an enzyme, so as to give the (R)-amide and the (S)-acid. In order to obtain the (R)-acid the (R)-amide is subsequently hydrolysed into the (R)-acid.

The aminonitrile represented by formula 4 is subsequently converted into the corresponding racemic amino acid amine. One suitable method is described, for instance, in GB-A-1548032, the disclosure of which is herein incorporated by reference. The aminonitrile is converted at a pH of between 11 and 14, preferably between 12.5 and 13.5, in the presence of a base and a ketone or aldehyde, optionally followed by hydrolysis of the intermediately formed Schiff base in the presence of water. Preferably, an alkali metal hydroxide, such as KOH or NaOH, or a corresponding base is used as the base and an aliphatic ketone, for example acetone, methyl ethyl ketone or cyclohexanone, or an aromatic aldehyde, for example benzaldehyde, is used as the ketone or aldehyde.

Aminonitrile obtained as formula 4 can be isolated via extraction from the aqueous phase using an organic solvent (e.g. aromatic hydrocarbons such as toluene, esters or chlorinated hydrocarbons), and separation of the two layers, if desired. The organic layer containing the aminonitrile may be dried to give the free amino acid nitrile or treated with e.g. HCl-gas in order to precipitate the (more stable) aminonitrile HCl salt.

A benzaldehyde is preferably used in the formation of the Schiff base of the amino acid amide. An advantage of benzaldehyde is that it is easy to separate the Schiff base and recover the benzaldehyde. The Schiff base of the amide is obtained as a precipitate and can be filtered off (and optionally converted into the free amide). Another advantage of benzaldehyde is that it is not miscible with water, and consequently it is also far more preferable than other extraction means because the thus formed Schiff base of the optically active amino acid amide dissolves in the benzaldehyde whereas the other components of the reaction mixture are in the water phase. It has surprisingly been found that the hydrolysis of the Schiff base of the amino acid amide to obtain the salt of the amino acid amide can be carried out without the acetal function deteriorating significantly.

'Benzaldehyde' is also understood to include substituted benzaldehydes such as lower (1–4 carbon atoms) alkylbenzaldehydes, halogenbenzaldehydes, nitrobenzaldehydes and lower (1–4 carbon atoms) alkoxybenzaldehydes.

The reaction with benzaldehyde resulting in the formation of a Schiff base can, for example, be carried at a temperature of between about 20° C. and about 60° C., preferably between about 35° C. and about 45° C. A precipitate of the Schiff base of the amino acid amide is obtained equimolar amounts of benzaldehyde, for example 0.9–2, in particular 0.95–1.1 equivalents relative to the amino acid amide, are used in the formation of the Schiff base without a different solvent for the Schiff base of the amide. The other components remain dissolved in the mother liquor. If an excess of benzaldehyde is used, the benzaldehyde acts both as a reaction means and as a solvent, and two layers are obtained. It is also possible to use mixtures of benzaldehyde and other solvents, for example mixtures with aromatic hydrocarbons, for example toluene, ketones, for example methyl isobutyl ketone, halogenated hydrocarbons, for example chloroform or dichloromethane; esters, for example ethyl acetate and butyl acetate. The organic phase can subsequently be used as such in the hydrolysis of the Schiff base of the amino acid amide to the amino acid amide or it can be subjected to concentration, upon which the Schiff base of the amino acid amide precipitates as a solid.

The amino acid amide can be recovered from the corresponding Schiff base in a simple manner, through acidification with a strong acid, for example sulphuric acid, until a pH of between 3 and 5, preferably between 3.5 and 4.5 has been obtained, with the Schiff base decomposing to form the aldehyde and the corresponding salt of the amino acid amide.

The free amino acid amide can subsequently be obtained from the salt through treatment with a base, for example with triethylamine. Preferably, the conversion of the salt into the free amino acid amide is carried out with the aid of a (strongly) basic ion exchanger, for example Amberlyst 26 or IRA 900.

The amino acid amide intermediates represented by formula 5 and the Schiff bases thereof that are represented by formula 6 are novel compounds.

(6)

In the formula 6, n is 0, 1, 2, 3 or 4; $R_1$ and $R_2$ each independently represent an alkyl group having 1–10 carbon atoms, or $R_1$ and $R_2$ form an akylene group whereby a ring is formed; and from 1 to 4 $R^i$ substituents are present, each $R^i$ being independently selected from among halogen, nitro, an alkyl group or an alkoxy group. Representative alkyl groups having 1–10 carbon atoms include, among others, methyl, ethyl n-propyl, butyl (n-butyl, sec-butyl, t-butyl), pentyl and cyclopentyl. Halogen substituents are, independent of one another, fluoro, chloro, bromo and, in principle, iodo. The $R^i$ groups are independent of one another. The above-mentioned ring is formed with 3–4 carbon atoms together with the oxygen atoms to which they are bound and the carbon atom to which the oxygen atoms are bound. The alkyl and alkoxy group for $R^i$ preferably contain 1–4 carbon atoms. The invention therefore also relates to these intermediates, both in racemic form and in optically active form, in particular the amino acid amides having an enantiomeric excess ("e.e.") greater than 80%, preferably greater than 90%, more preferably greater than 95%, most preferably greater than 98%, in particular greater than 99%.

The racemic (R,S) amino acid amide is subsequently subjected to an enantioselective, enzymatic hydrolysis in which the (S)-enantiomer is selectively converted into the corresponding (S)-acid and the (R)-amide enantiomer remains unaffected. The (R)-amide may subsequently be hydrolyzed into the (R)-acid. Also, the (S)-amide could be obtained using a D-amidase, as described in Yasuhisa Asano et al. Biochemical and Biophysical Research Communications, Vol 162, No. 1, 1989, p 470–474, or alternatively, via esterification and amidation of the (S)-amino acid. The (S)-2-amino-ω-oxoalkanoic acid derivative can then be obtained with an e.e. of more than 90%, in particular more than 95%, preferably more than 98%, in particular more than 99%. The enantioselective enzymatic hydrolysis is preferably carried out in an aqueous environment. It is however also possible to use an organic solvent. The temperature is not particularly critical and lies, for example, between about 0° C. and about 60° C., preferably between about 20° C. and about 50° C. The pH at which the enzymatic hydrolysis is carried out is preferably between 5 and 10.5, in particular between 8.0 and 9.5. Suitable, amidase enzymes for example, are available, and include, an amidase derived from the genus Asperpillus, Mycobacterium, Aeromonas, Bacillus, Pseudomonas or Ochrobactrum. Preferably, an amidase derived from *Pseudomonas putida* or from *Ochrobactrum anthropi* is used.

After, for example, the removal of the (R)-enantiomer of the amino acid amide as the Schiff base, or concentration and treatment with alcohol, for example isopropanol, the optically active (S)-2-amino-ω-oxoalkanoic acid derivative can be obtained. The Schiff base of the (R)-enantiomer of the amino acid amide can, optically, be converted into the free amino acid amide, which in turn can optionally be hydrolyzed under mild conditions, for example via a (non-stereoselective) enzymatic hydrolysis as described in EP-A-179523, the disclosure of which is herein incorporated by reference, using *Rhodococcus erywhronolis* or an extract thereof, to obtain the (R)-2-amino-ω-oxoalkanoic acid derivative. The optically active (R)-2-amino-ω-oxoalkanoic acid derivatives are novel compounds with various applications. The compounds represented by formula 7

(7)

are, for example, particularly suitable for use in the preparation of D-pipecolic acid derivatives such as, for example, described in J.O.C. (1990), 5551–3, and in Bioorg. & Med. Chem. (1995), 1237–1240, the disclosures of which are both herein incorporated by reference, which are in turn used per se in the preparation of various pharmaceuticals such as, for example, described in EP-A-672665, DE-A-3702943 and U.S. Pat. No. 5,409,946, the disclosures of all three being herein incorporated by reference. The compounds represented by formula 7 can also be used as an intermediate(s) in the preparation of D-proline, which is used, for example, in the preparation of Elitriptan as described in 'Drugs of the Future' (1997), 221–223, the disclosure of which is herein incorporated by reference. The invention also relates to these novel compounds, in particular to the optically active (R)-2-amino-ω-oxoalkanoic acid derivatives having an e.e. greater than 80%, preferably greater than 90%, in particular greater than 95%.

Figure 3A:
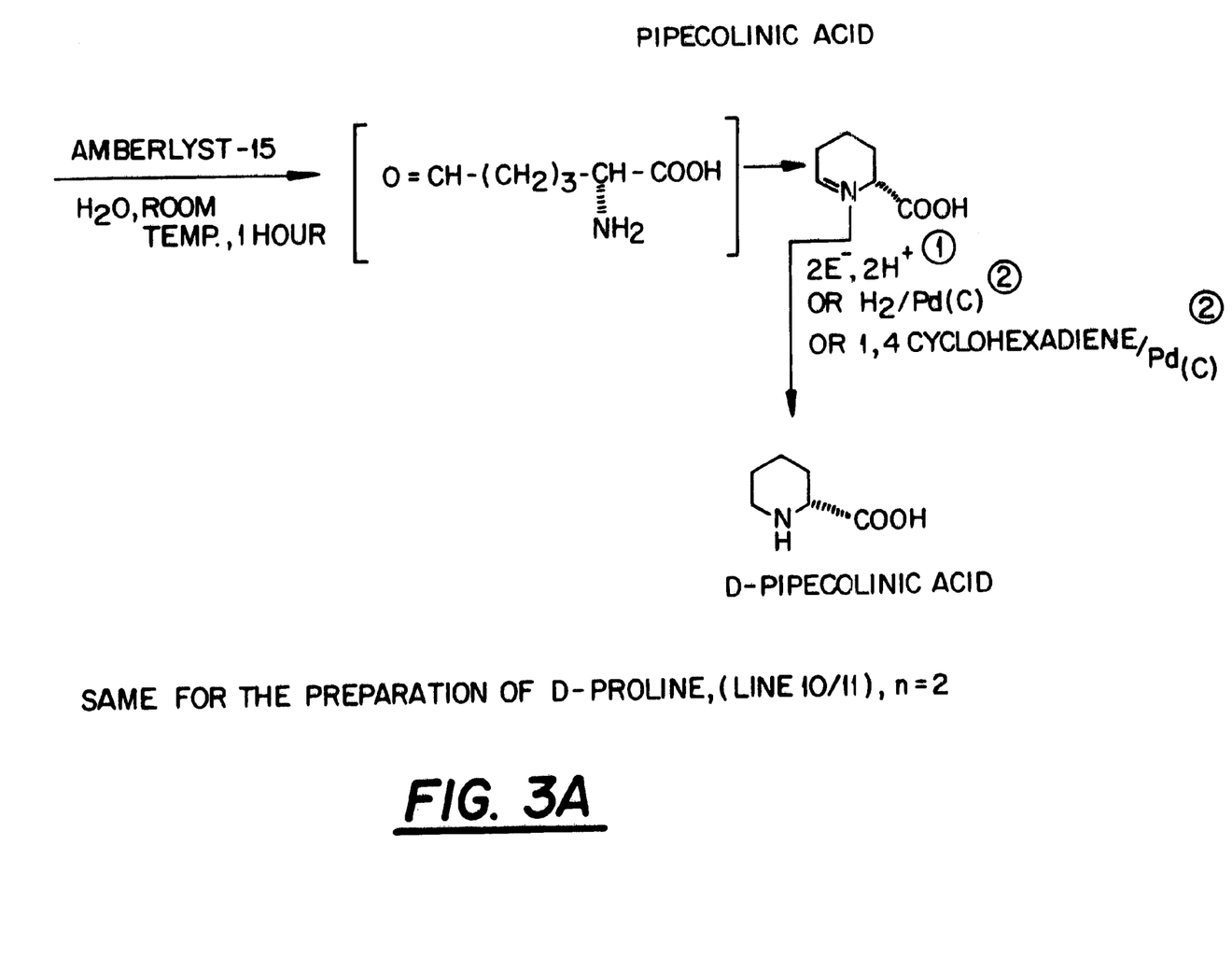
FIG. 3 is a reaction scheme using D-proline.
Figure 3B:
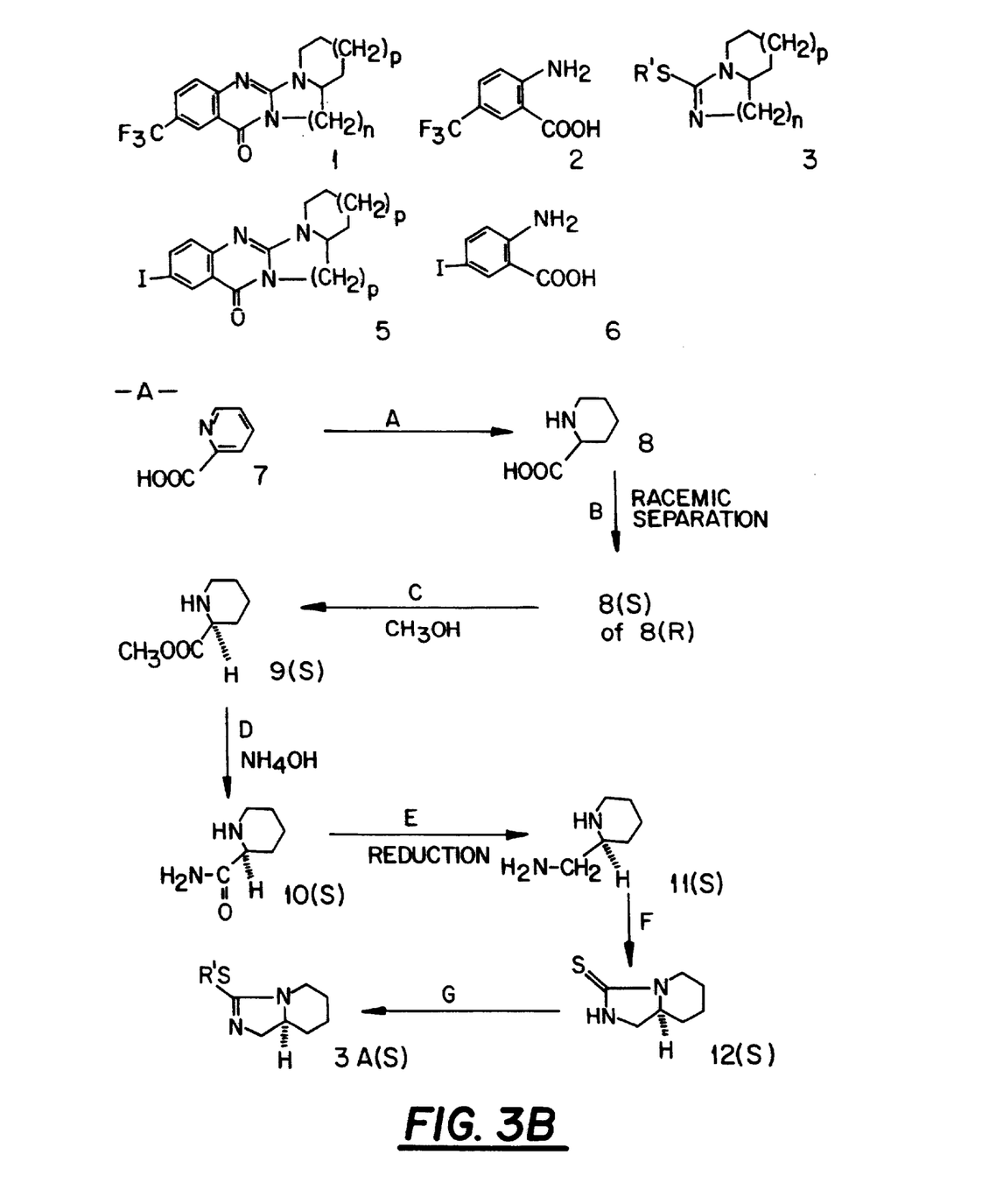
Figure 3C:
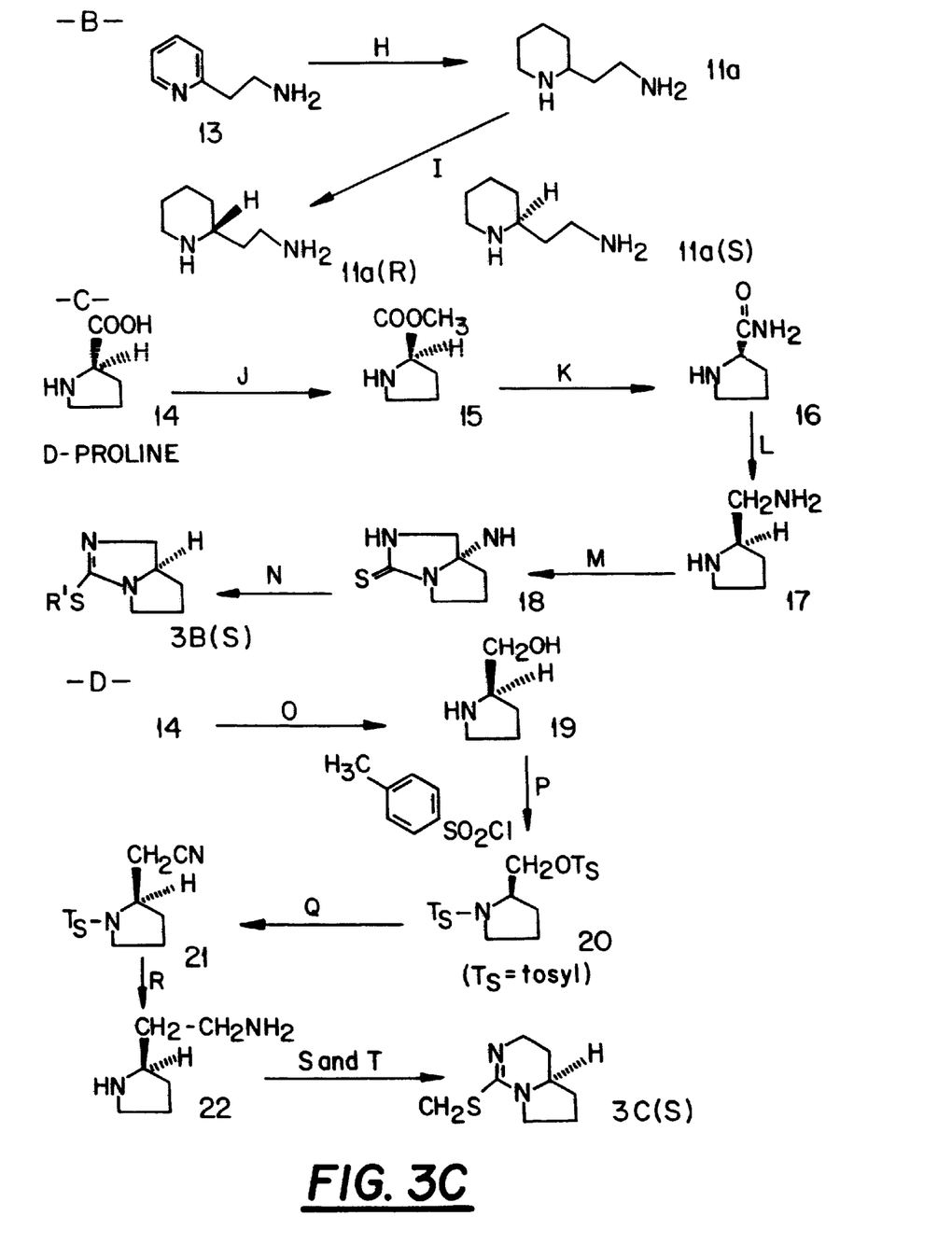

The preparation of D-pipecolic acid and D-proline, referred to above in principle analogous. Reaction schemes are shown in FIG. 3. The subject matter of B. Ohtani et al., J. Org. Chem. (1990), 55, 5551–5553, and T. F. Buckley and H. Rapaport, J. Am. Chem. Soc. (1982) 104, 4446–4450, referred to in FIG. 3 is also incorporated herein by reference.

An application of these compounds is given in FIG. 3. According to FIG. 3–2 and FIG. 3—3, compound 9 (obtained from the formula 1 compound with n=3) is converted in 10, 11, 12, and 3 subsequently and compound 3 is, together with compound 2 converted into compound 1, shown in FIG. 3–2.

The use of D-proline is demonstrated in FIG. 3—3 wherein compound 14 represents D-proline.

The description of the invention in Netherlands Application 1007113, filed Sep. 25, 1997 is incorporated herein by reference.

DETAILED DESCRIPTION OF THE PREFERRED EMBODIMENTS

The invention will now be elucidated with reference to the examples without being limited thereby.

EXAMPLES

Example I

Preparation of 4-(1.3-dioxolane-2-yl)-1-butanal via the Acetalization of Glutaraldehyde with Ethylene Glycol Toluene (1 liter), ethylene glycol (155 grams, 2.5 mol) and p-toluenesulphonic acid (1 gram) were successively dosed to a 50% solution of gluardialdehyde in water (500 grams, 2.5 mol). The mixture was heated to reflux temperature. The water was azeotropically removed with the aid of a Dean-Stark apparatus. As soon as all the water had been removed with the aid of the Dean-Stark apparatus (approx. 6 hours) the solution was cooled to room temperature.

Sodium bicarbonate (2.1 grams) and water (250 ml) were added to the solution. After vigorous stirring for half an hour the layers were separated. This washing of the toluene phase was repeated twice. Then the toluene phase was evaporated in a rotary film evaporator to obtain a pale yellow oil. The 4-(1,3-dioxolane-2-yl)-1-butanal content was 50% (G.C.) with a yield 5 of 35%.

Example II

Preparation of the Schiff base of 2-amino-5-(1,3-dioxolane-2-yl)-pentanoic Acid Amide via the Strecker Reaction of 4-(1,3-dioxolan-2-yl)-1-butanal Sodium cyanide (49 grams, 1 mol) and ammonium acetate (77 grams, 1 mol) were successively added to a 25% solution of ammonia in water (500 ml). The oil obtained in Example I (288 grams, 1 mol) was added dropwise to this solution over a period of one hour. After further stirring for 5 hours, acetone (100 ml) and a 45% solution of potassium hydroxide in water (10 ml) were successively dosed to this solution. After 3 hours glacial acetic acid (7 ml) was added. The solution was concentrated to approx. 400 grams with the aid of a rotary film evaporator to obtain a concentrate. Water (600 ml) and toluene (150 ml) were added to the concentrate. After stirring for half an hour layers were separated. Benzaldehyde (74 grams) was slowly dosed to the water phase with vigorous stirring. The white precipitate formed was removed base of 2-amino-5-(1,3-dioxolane-2-yl)-pentanoic acid amide was 195 grams (yield 70%) at a purity>98% ($^1$H-NMR).

Example III

Preparation of (S)-2-amino-5-(1,3-dioxolane-2-yl)-pentanoic Acid via the Enzymatic Resolution on 2-amino-5-(1,3-dioxolane-2-yl)-pentanoic Acid Amide The Schiff base of 2-amino-5-(1,3-dioxolane-2-yl)-pentanoic acid amide (240 grams, 0.87 mol) was suspended in toluene (1000 ml) and water (1500 ml). Concentrated sulphuric acid (44.5 grams, 0.44 mol) was very slowly dosed with vigorous stirring, so that the pH remained above 4.0. After the dosage of the sulphuric acid the layers were separated. The water phase was subsequently passed over a strongly basic ion exchanger (type IRA 900). The sulphate-free water phase was subsequently brought to a pH of 9.0 with acetic acid. *Pseudomonas putida* (obtained from NOVO) (40 grams) was added to this solution. After stirring at 37° C. for 8 hours, decalite (30 grams) and, dropwise, benzaldehyde (51 grams, 0.48 mol) were successively dosed to the suspension. The precipitate formed was removed with the aid of filtration. The filtrate obtained was concentrated to about 450 grams with the aid of a rotary film evaporator. After heating to 65° C. isopropanol (900 grams) was added to the solution. After slow cooling to −5° C. the white crystals formed were filtered and successively washed with ice water and isopropanol. The yield of (S)-2-amino-5-(1,3-dioxolane-2-yl)-pentanoic acid was 42 grams (26%). The melting point was 258° C., the purity was >99% (titration), and the e.e % was greater than 99% (HPLC).

Example IV

Preparation of (S)-2-amino-5-(1,3-dioxolane-2-yl)-pentanoic Acid via the Enzymatic Resolution on 2-amino-5-(1,3-dioxolane-2-yl)-pentanoic acid Amide Glacial acetic acid was added to the water phase obtained after the toluene extraction (see Example II ) so that the pH became 9.0. At 37° C. *Pseudomonas putida* (obtained from NOVO) was added to this water phase. After stirring for 8 hours, the water phase was treated as described in Example III. The yield of (S)-2-amino-5-(1,3-dioxolane-2-yl)-pentanoic acid was 11%, the purity was 95% (HPLC), and the e.e. % was >99% (HPLC).

Example V

Preparation of (S)-2-amino-5-(1,3-dioxolane-2-yl) pentanoic Acid via the Enzymatic Resolution on 2-amino5-(1.3-dioxolane-2-yl)-pentanoic acid Amide The water phase obtained after the hydrolysis of the Schiff base with sulphuric acid (see Example III) was brought to a pH of 9.0 with the aid of triethylamine. At 37° C., *Pseudomonas putida* (obtained from NOVO) was subsequently dosed to this solution. After stirring for 8 hours, the thus obtained suspension was processed further as described in Example III. The yields of (S)-$^2$-amino-5-(1,3-dioxolane-2-yl)-pentanoic acid was 24%. The purity was 76% (HPLC) and the e.e. % was greater than 99% (HPLC).

What we claim is:

1. The 2-aminonitrile represented by formula 4

(4)

wherein n equals 0, 1, 2, 3 or 4 and $R_1$ and $R_2$ each independently represent an alkyl group with 1–10 carbon atoms or form a ring with 3 or 4 carbon atoms together with the oxygen atoms to which they are bound.

2. The 2-aminonitrile according to claim 1, wherein n equals 2 or 3.

3. A compound according to any one of claim 1, wherein $R_1$ and $R_2$ form a ring with 3 or 4 carbon atoms together with the oxygen atoms to which they are bound and the carbon atom to which the oxygen atoms are bound.

4. The 2-aminonitrile according to claim 1, prepared by a method comprising:

converting the corresponding aldehyde represented by formula 2

(2)

wherein n equals 0, 1, 2, 3 or 4, with the aid of an alcohol, a diol or an orthoformate ester into the corresponding acetal-protected aldehyde represented by formula 3

(3)

with n as described above and $R_1$ and $R_2$ each independently represent an alkyl group with 1–10 carbon atoms or form a ring with 3 or 4 carbon atoms together with the oxygen atoms to which they are bound and the carbon atom to which the oxygen atoms areas bound, converting the acetal-protected an dehyde into the corresponding aminonitrile represented by formula 4

(4)

with n, $R_1$ and $R_2$ as described above, the conversion occurring in the presence of ammonia with the aid of a cyanide compound, and isolating the 2-aminonitrile from an aqueous phase using an organic solvent.

5. The 2-aminonitrile according to claim 4, wherein an organic layer containing the aminonitrile is dried to yield a free amino acid nitrile.

6. The 2-aminonitrile according to claim 4, wherein an organic layer containing the aminonitrile is treated with an acid gas to precipitate an aminonitrile acid salt.

7. The 2-aminonitrile prepared according to the method of claim 4, wherein the 2-aminonitrile is isolated via extraction.

* * * * *